US006180845B1

(12) United States Patent
Catallo et al.

(10) Patent No.: US 6,180,845 B1
(45) Date of Patent: Jan. 30, 2001

(54) TRANSFORMING BIOMASS TO HYDROCARBON MIXTURES IN NEAR-CRITICAL OR SUPERCRITICAL WATER

(75) Inventors: W. James Catallo, Baton Rouge; Thomas Junk, Monroe, both of LA (US)

(73) Assignee: Board of Supervisors of Louisiana State University and Agricultural and Mechanical College, Baton Rouge, LA (US)

( * ) Notice: Under 35 U.S.C. 154(b), the term of this patent shall be extended for 0 days.

(21) Appl. No.: 09/414,755

(22) Filed: Oct. 7, 1999

(51) Int. Cl.[7] ............................. C07C 1/00; C02F 11/10

(52) U.S. Cl. ........................................ 585/240; 585/242

(58) Field of Search .................... 585/240, 241, 585/242; 201/2.5, 25

(56) References Cited

U.S. PATENT DOCUMENTS

| | | | |
|---|---|---|---|
| 5,516,952 | 5/1996 | Lee et al. | 585/241 |
| 5,589,599 | * 12/1996 | McMullen et al. | 585/240 |
| 5,830,763 | 11/1998 | Junk et al. | 436/56 |
| 6,084,147 | * 7/2000 | Mason | 588/19 |

OTHER PUBLICATIONS

Baker, E. et al., "Characteristics of hydrothermal plumes from two vent fields on the Juan de Fuca Ridge, northeast Pacific Ocean," *Earth & Planetary Sci. Lett.*, vol. 85, pp. 59–73.

Catallo, W., "Hydrocarbon Transformation in High Energy Aqueous Systems," copies of slides presented at 25th Annual Conference of the Federation of Analytical Chemistry and Spectroscopy Societies (Oct. 11–15, 1998, Austin, Texas).

Catallo, W., "Hydrocarbon Transformation in High Energy Aqueous Systems: Analytical and Mechanistic Challenges, "Final Book of Abstracts, 25th Annual Conference of the Federation of Analytical Chemistry and Spectroscopy Societies (Oct. 11–15, 1998, Austin, Texas).

Catallo, W. et al., "Sonochemical dechlorination of hazardous wastes in aqueous systems," *Waste Management*, vol. 15, pp. 303–309 (1995).

Didyk, B. et al., "Hydrothermal oil of Guaymas Basin and implications for petroleum formation mechanisms," *Nature*, vol. 342, pp. 65–69 (1989).

Goetz, F. et al., "Aromatic hydrocarbon–degrading bacteria in the petroleum–rich sediments of the Guaymas Basin hydrothermal vent site: preference for aromatic carboxylic acids," *Geomicrobiology J.*, vol. 11, pp. 1–8 (1993).

(List continued on next page.)

Primary Examiner—Bekir L. Yildirim
(74) Attorney, Agent, or Firm—John H. Runnels

(57) ABSTRACT

Reacting organic compounds with near-critical or supercritical aqueous phases can dramatically transform the organic compounds over short time periods (on the order of minutes to hours). The reductive process is conducted in anaerobic or near-anaerobic conditions. The process works with a wide range of organic compounds and biomass sources, including cellulose, chitin, starches, lipids, proteins, lignin, and whole cells. Disposal of waste biomass is currently expensive, and can create environmental problems. The present invention allows the conversion of waste lipids (for example) into a hydrocarbon mixture similar to a sweet crude petroleum, along with volatile alkane and alkene gases ($C_2$ to $C_5$). This conversion allows the generation of a burnable fuel, as well as the generation of feed streams for reforming and distillation. The environmental and other costs associated with fossil fuel extraction are reduced. Reactions in accordance with the present invention may be conducted in continuous, batch, or semi-batch mode. To date, we have used both batch and stop-flow reactors to transform biomass in near-critical (320–390° C., 200–420 bar) and supercritical water (400–500° C., 400–550 bar).

20 Claims, 1 Drawing Sheet

OTHER PUBLICATIONS

Junk, T. et al., "Hydrogen isotope exchange reactions involving C–H (D, T)," *Chem. Soc. Rev.*, vol. 26, pp. 401–406 (1997).

Junk, T. et al., "Preparative supercritical deuterium exchange in arenes and heteoarenes," *Tetrahedron Letters*, vol. 37, pp. 3445–3448 (1996).

Junk, T. et al., "Synthesis of polydeuterated benzothiazoles via supercritical deuteration of anilines," *J. Labelled Compounds and Radiopharmaceuticals*, vol. 39, pp. 625–630 (1997).

* cited by examiner

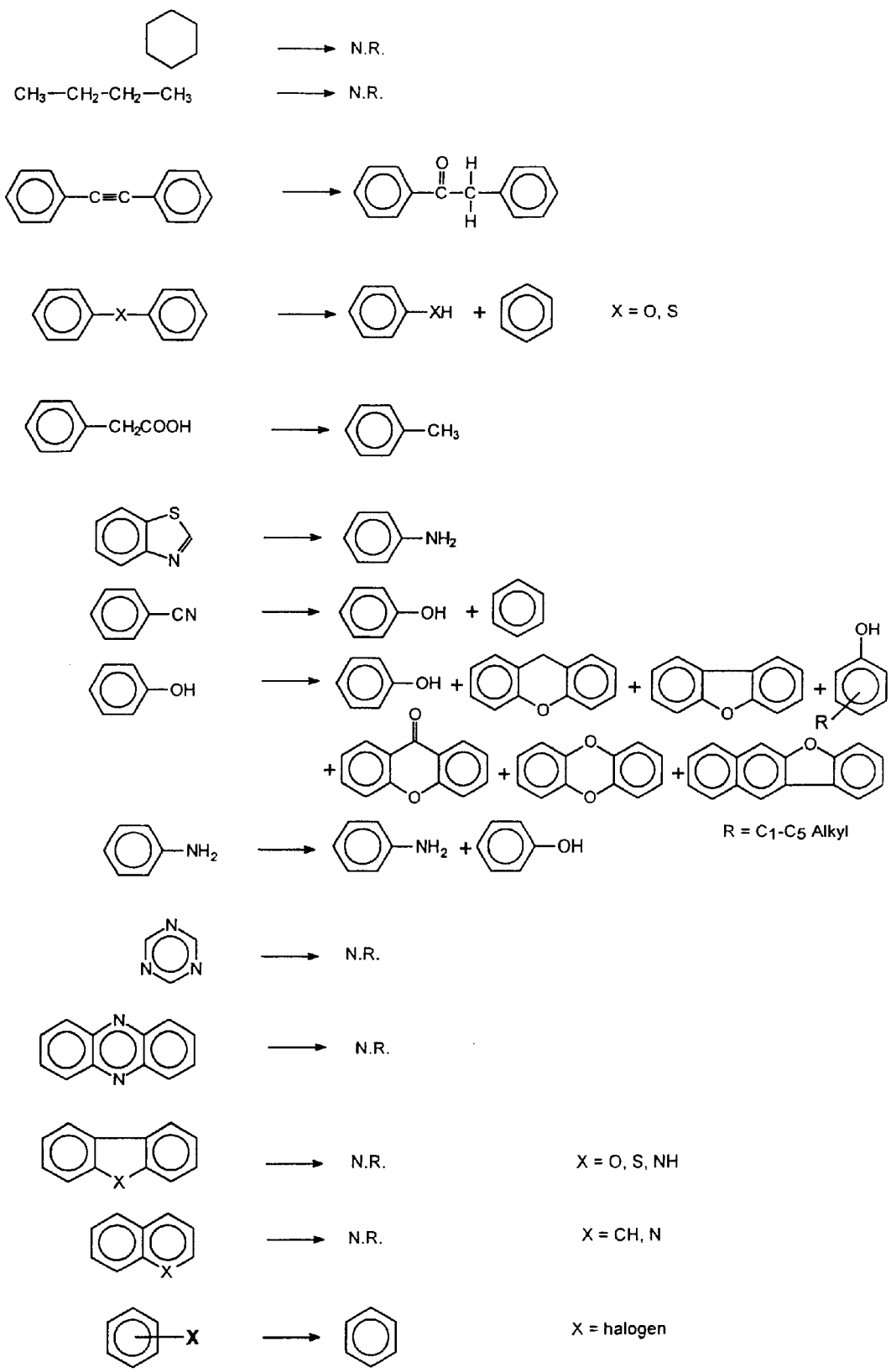
FIGURE

TRANSFORMING BIOMASS TO HYDROCARBON MIXTURES IN NEAR-CRITICAL OR SUPERCRITICAL WATER

This invention pertains to a method for transforming biomass, such as waste of biological origin, into useful products, particularly to a method for transforming biomass to petroleum-like hydrocarbon mixtures by reaction with water under supercritical or near-critical reaction conditions.

Above a fluid's so-called critical pressure and critical temperature, the distinction between liquid and gas phases vanishes, and instead one finds a single "supercritical" fluid phase with unique properties. The critical temperature for pure water is 374.2° C., and its critical pressure is 221 bar. Near-critical water has properties that are similar in many respects to those of supercritical water, but can be characterized by two phases: (1) a relatively dense, hot, vapor phase; and (2) a relatively less dense (~0.5–0.8 g/cc), hot fluid phase. Typical near-critical and supercritical aqueous phases have temperatures and pressures in the range from about 320° C. to about 500° C. (or higher) and greater than about 200 bar.

U.S. Pat. No. 5,516,952 discloses a process for breaking down natural, synthetic, vulcanized, and non-vulcanized rubbers by selective oxidation in supercritical or near critical water with an oxidant such as air, oxygen, or other oxidizing agent. Typical products were said to include alkanes, alkenes, dienes, aromatics, alcohols, carboxylic acids, aldehydes, and ketones, all preferably having from about 3 to about 8 carbon atoms, as well as carbon dioxide, water, and halide acids.

The current inventors' own U.S. Pat. No. 5,830,763 discloses a process for the preparation of organic and inorganic deuterium-tagged compounds by heating with deuterium oxide under supercritical conditions. See also T. Junk et al., "Synthesis of polydeuterated benzothiazoles via supercritical deuteration of anilines," *J. Labelled Compounds and Radiopharmaceuticals*, vol. 39, pp. 625–630 (1997); and T. Junk et al., "Preparative supercritical deuterium exchange in arenes and heteroarenes," *Tetrahedron Letters*, vol. 37, pp. 3445–3448 (1996); and T. Junk et al., "Hydrogen isotope exchange reactions involving C—H (D, T)," *Chem. Soc. Rev.*, vol. 26, pp. 401–406 (1997).

W. Catallo et al., "Sonochemical dechlorination of hazardous wastes in aqueous systems," *Waste Management*, vol. 15, pp. 303–309 (1995) discloses the use of ultrasonic processes to dechlorinate certain organic compounds.

W. Catallo, "Hydrocarbon Transformation in High Energy Aqueous Systems," copies of slides presented at 25th Annual Conference of the Federation of Analytical Chemistry and Spectroscopy Societies (Oct. 11–15, 1998, Austin, Tex.) discusses some material from an early phase of the work disclosed in the present specification.

W. Catallo, "Hydrocarbon Transformation in High Energy Aqueous Systems: Analytical and Mechanistic Challenges," Final Book of Abstracts, 25th Annual Conference of the Federation of Analytical Chemistry and Spectroscopy Societies (Oct. 11–15, 1998, Austin, Tex.) gave only the title of that presentation.

B. Didyk et al., "Hydrothermal oil of Guaymas Basin and implications for petroleum formation mechanisms," *Nature*, vol.342, pp. 65–69 (1989) discloses that petroleum-like hydrocarbons had been found in association with certain submarine hydrothermal vent emissions in the Gulf of California, and that those hydrocarbons had a carbon-14 date of 4200–4900 years. The authors stated that the oil expulsion and migration mechanisms were provided by the hydrothermal fluids under pressures of 200 bar and temperatures up to and exceeding 315° C. at some vent outlets; and speculated that there were probably near-critical conditions further down the sedimentary column. See also F. Goetz et al., "Aromatic hydrocarbon-degrading bacteria in the petroleum-rich sediments of the Guaymas Basin hydrothermal vent site: preference for aromatic carboxylic acids," *Geomicrobiology J.*, vol. 11, pp. 1–8 (1993).

E. Baker et al., "Characteristics of hydrothermal plumes from two vent fields on the Juan de Fuca Ridge, northeast Pacific Ocean," *Earth & Planetary Sci. Lett.*, vol. 85, pp. 59–73 (1987) discusses the physical characteristics of hydrothermal plumes on the Juan de Fuca Ridge.

We have discovered that reacting organic compounds in near-critical or supercritical aqueous phases can dramatically transform the organic compounds over short time periods (on the order of minutes to hours) into petroleum-like hydrocarbon mixtures. The reductive process is conducted in anaerobic or near-anaerobic conditions, essentially free of any strong oxidants. Optionally, strong reducing agents or other co-reactants may be added to tailor product distributions. The novel process works with a wide range of organic compounds and biomass sources, including cellulose, chitin, starches, lipids, proteins, lignin, and whole cells.

The starting materials used in this process can come from a wide variety of sources, many of which would otherwise be waste materials, including by-products of food manufacture and distribution (e.g., fryer oils; waste scraps; last-press edible oils such as canola and olive oils, food processing wastes, seafood industry wastes); by-products of paper and other wood industry manufacturing (e.g., cellulose and lignin by-products); yard waste such as leaves and grass clippings; rice hulls; bagasse; seaweed; milling waste; cotton waste; animal waste. Disposal of these wastes is currently expensive, and can create environmental problems. For example, food oils currently are typically disposed as high biological-oxygen-demand wastes in aerobic digesters or other treatment systems, such as ponds or lagoons. Aerobic digester disposal is expensive, and the carbon dioxide generated is not accompanied by the evolution of usable energy. Effluents from aerobic digesters can cause eutrophication and impaired ecological function in rivers and wetland systems.

The present invention allows the conversion of waste lipids (for example) into a hydrocarbon mixture similar to a sweet crude petroleum, containing (for example) volatile alkane and alkene gases ($C_2$ to $C_{10}$) and liquid hydrocarbon mixtures. This conversion allows the generation of a burnable fuel, as well as the generation of feed streams for reforming and distillation. The environmental and other costs associated with traditional fossil fuel extraction are reduced.

It has been estimated that the world will have consumed most known and projected sources of available crude petroleum within the next 70–100 years. Some of the resulting shortfall could be mitigated economically by using the present process to produce petroleum-like products and related materials (e.g., lubricants) from materials that are otherwise considered waste products. To reduce environmental impact further, it is preferred (though not required) that the energy used to create the supercritical conditions be obtained from an environmentally-friendly source, such as collimated and focused solar energy, geothermal energy, or electrical energy produced by co-generation at an industrial plant.

Reactions in accordance with the present invention may be conducted in continuous, batch, or semi-batch mode. To date, we have used both batch and stop-flow reactors to transform biomass in near-critical (320–390° C., 200–420 bar) and supercritical water (400–500° C., 400–500 bar). The biomass starting materials that we have used in prototype experiments to date have includedd lipids, nucleic acids, starch, protein, algae, whole plant matter, cellulose, chitin, humic acid, and lignin. Other starting materials that could be used include biological laboratory wastes (cells, media, etc.), and modified mixtures such as synthetic oils, pharmaceutical and medical wastes, and naturally occurring organic mixtures such as peat, partially decayed leaf litter, kerogen, etc. Typical reaction times under near-critical and supercritical conditions were one to eight hours.

BRIEF DESCRIPTION OF THE DRAWING

The FIGURE depicts reactions that have been previously observed for various synthetic organic chemical functionalities in supercritical water.

All starting biogenic materials we have tested were transformed under near-critical and supercritical conditions to complex semivolatile mixtures containing monoaromatics (e.g., benzene, phenol), polyaromatic hydrocarbons (PAHs) (e.g., naphthalene), and their $C_1$–$C_5$ alkyl homologs (i.e., the listed compounds with $C_1$–$C_5$ alkyl substituents). Other products included gases (e.g., $CO_2$, $CH_4$, and a complex mixture of volatile olefins and paraffins), asphaltic compounds, and carbonized residues. The principal semi-volatile components of the reaction products were monoaromatic compounds: benzene and $C_1$–$C_5$ alkyl substituted benzenes (e.g., toluene, xylenes, etc.). A major difference between the near critical and supercritical treatments was that supercritical conditions produced higher yields of both gaseous hydrocarbons and insoluble carbonized residue.

Factors that we have observed to influence the composition and concentration of products generated by reacting biomass in near critical and supercritical aqueous phases included the following: (a) the elemental composition and molecular structures of the starting materials, (b) the temperature, (c) the duration of exposure to near critical and supercritical water, (d) the presence of metals such as iron or nickel in the reaction mixture, and (e) the presence of additional reactants in the reaction system, including inert substances (e.g., Ar), other co-reactants, and reactive substances (e.g., $H_2$ gas, $Na_2H_2BO_4$ powder).

The elemental composition of the starting materials can affect the nature of the products generated. For example, the presence of significant amounts of nitrogen can in some cases give rise to the formation of amines and N-heterocyclic compounds; and the presence of significant amounts of sulfur can in some cases give rise to the formation of S-heterocyclic compounds. These compounds, while undesirable in large concentrations, are present in many crude petroleums refined today (e.g., Saudi, North Slope, Siberian, Ecuadorian), and existing scrubbing technologies can be used to remove them. Also, treatment conditions can be adapted to preferentially remove these materials (e.g., Cu powder for sulfur compounds, acidification or precipitation with metals for nitrogen compounds). In the samples we have tested to date, heteroatoms were present in significant amounts, for example, in pure DNA samples, pure protein samples, and in a yeast sample. (The latter is an organism that synthesizes compounds with high nitrogen content).

The time and the temperature of the treatment affected the formation of reaction products. In general, above the critical point an increase in temperature gave rise to decreases in particulate and semi-volatile (liquid) yields, and increases in gaseous product yields (volatile hydrocarbons). Thus higher temperatures can be used for short-duration treatments (e.g., flow through and pulsed systems), or to generate larger amounts of $C_1$–$C_{10}$ volatiles. Below the critical point (i.e., near critical reaction conditions), increases in treatment time tended to mimic the short term SC treatments. Increasing duration generally caused more gas formation, and decreased semivolatile liquid recovery.

We observed that the presence of metals in the reaction system greatly reduced the complexity of the semi-volatile and volatile product mixture. The use of quartz-lined reactors avoided this effect, retaining a more complex product mixture. Metals can be used where desired to simplify the components of the product mixture, or to precipitate unwanted products (e.g., using Cu to remove thiophenes). Titanium reactors have also been used for reactions involving very acidic and very basic media.

The near critical or supercritical reaction system should be anoxic or as close to anoxic as is reasonably feasible under the circumstances. Otherwise, some carbon is lost as $CO_2$ or CO. Ar and other inert gases facilitate deoxygenation of the systems, and can be recovered and purified for reuse. Reactant gases such as $H_2$ are used to promote saturation reactions and to lower aromatic content. Reducing agents such as sodium borohydride cause the product mixture to become gel-like and dichloromethane-insoluble (similar to a lubricating oil or petroleum jelly). Yields of volatiles and semivolatiles decreased substantially in the presence of this sodium borohydride.

Homogenization of solid samples prior to treatment greatly facilitated the generation of desirable volatile and semivolatile materials, and reduced or almost eliminated the production of solid particulates in the product mixtures.

Because biomass starting materials may contain certain pollutants (e.g., pesticides, fertilizers, and additives in agricultural and food industry wastes), it is useful to know that reaction conditions in supercritical water will alter some, but not all organic functional groups. The FIGURE depicts reactions that have been previously observed for various synthetic organic chemical functionalities in supercritical water at ~400° C. and ~285 bar for 12 or 24 hours. "N.R." indicates that no reaction was observed.

Materials and Methods

Reactors were fabricated from high-nickel steel alloys with quartz liners, in volumes ranging from 50 to 2000 mL. (GE high purity grade quartz 214A; 1.0 mm wall thickness). The samples were introduced into the vessels to an internal volume of about 50–60%, evacuated, and sealed with a metal-metal compression seal. This arrangement allowed near critical and supercritical reactions in the absence of surface reactions or solution reactions involving metals from the steel reactor. The reactors were placed in pre-heated muffle furnaces for total reaction times of 1–24 hours. Internal pressures were estimated using P-V-T curves for pure water or brines as appropriate.

The aqueous and particulate phases then were recovered from cooled reactors, placed in separatory funnels, and extracted three times with methylene chloride. The extracts then were combined and dried over anhydrous sodium sulfate. The different fractions were analyzed as follows: The head space over the slurry was analyzed by GC-MS for volatile compounds (namely, compounds with a molecular weight under 78.) The methylene chloride phase was analyzed by GC-MS for semi-volatile compounds (namely, those in a molecular weight range from 78–276). The aqueous phase was analyzed by capillary electrophoresis. The residual particulate phase was weighed, but was not further analyzed.

Analyses of the extracts were performed by gas chromatography-mass spectrometry (GC-MS) in the full scan mode. Chromatographic conditions were as follows: Shimadzu QP500 GC-MS; DB-5MS capillary column (30 m; 0.25 mm id; 0.25 μm film); injector 250° C. splitless; temperature program 50° C. (4 min), ramp 4–6° C./ min to 280° C. (5–20 min); sampling rate 4 Hz; and mass acquisition range 40–350 amu in the full scan mode. This range spanned the molecular weight range between benzene (78 amu) and benzoperylene and its isomers (276 amu). Product identification was performed by (a) comparison of experimental data with standards and computer databases of standards, and (b) interpretation of mass spectra (molecular ions, isotopic structures, low mass ion series). Extraction and solvent blanks were run routinely, and mass spectra were interpreted only when the total ion currents had at least a 3:1 signal/noise ratio.

Dried samples of biomass starting materials were weighed into crucibles (except that corn oil was dispensed and weighed as a liquid), and elemental analyses were performed on the starting materials for C, H, N, and S using a Perkin Elmer 2400 Series II CHNS/O Analyzer. A standard used for the elemental analyses was 2,5-bis-(5-tert-butyl-2-benzo-oxazole-2-yl)-thiophene, which has a C:H:N:O:S ratio of 72.52:6.09:6.51:7.43:7.44. All elemental analyses were replicated three times using fresh material taken from a bulk sample. The results are reported in Table 1 as percent C, H, N, S on a weight basis. Elemental analyses of the end products of two different reactions with a corn oil starting material are given in Table 2.

Results

Upon reaction in near critical and supercritical water, all the forms of biomass starting materials tested were rapidly transformed into mixtures of aliphatic and aromatic, volatile and semivolatile hydrocarbons that resembled crude petroleum. Volatile and semivolatile hydrocarbon yields were typically on the order of 60% or more, depending on reaction conditions and times.

Preferred reaction conditions were to place the biomass and water under a head space pressure of $H_2$ greater than ~65 bar, and then heat the reaction system to a temperature of ~400±20° C. for ~4 hours (not including the heating up and cooling down periods) under a head pressure of ~100 bar to ~300 bar.

When various biomass samples (intended to be typical of biomass waste from the food, paper, and agricultural industries) were reacted with near critical or supercritical water, the products exhibited generally similar structural features (e.g., extended alkyl homologies on series of mono-aromatic compounds). These products were also generally similar to those produced by low temperature diagenetic reactions that equilibrate in sediments over tens of thousands of years (i.e., petroleum).

In general, phenol, benzene, and their alkyl-substituted homologs were the most stable compounds generated. These structures may represent a confluence point in various reaction routes leading to high molecular weight products, e.g.:

biomass precursor (e.g., biopolymers)→substituted benzenes and phenols→PAHs→asphaltenes, soot, carbonized residues The initial reactions are degradative, and are accompanied for example by the production of $CO_2$, $CO$, $CH_4$, $H_2$ and light alkanes and alkenes ($C_1$ to $C_{10}$).

Extended near critical and supercritical treatment (e.g., 36–72 h) continued the condensation and disproportionation reactions, yielding primarily polymers, asphaltenes, and carbonized residues. Thus, the ultimate endpoint from most starting materials under these conditions was $C_1$ to $C_{10}$ gas generation or carbonization (i.e., soot and polymeric mixtures). With sufficiently long reaction times in near critical and supercritical water (~12 hours or more), even highly stable compounds (e.g., humic acid) were transformed to petroleum-like residues.

Representative starting and ending materials are depicted below:

| Starting Material | Ending Materials |
|---|---|
| corn oil (liquid) | petroleum-like liquid and volatile gases (very clean/sweet) |
| cellulose (solid) | petroleum-like liquid, volatile gases, and particulate residue |
| cells (solid/liquid) (e.g., plankton, yeast, bacteria, protozoa, fungi, monera, from, e.g., biotech and medical waste) | petroleum-like liquid, volatile gases, and particulate residue |

Homogenization of particulates and solids in the starting materials reduced the amount of particulate residue produced, and increased the amount of the petroleum-like liquid and volatile gases.

GC-MS spectra showed that the reaction products from the diatom *T. weissflogii* (a low nitrogen starting material) were particular high in $C_3$ to $C_6$-substituted benzenes, and $C_1$ to $C_3$-substituted phenols.

Reaction products from starch (a low nitrogen starting material) were particularly high in phenol, $C_1$ and $C_2$-substituted phenols, $C_1$ to $C_4$-substituted benzenes, $C_1$-substituted naphthalenes, $C_1$-substituted 1H-indenes, and unsubstituted and $C_1$ and $C_2$-substituted dihydro-1H-indenes.

Reaction products from humic acid (a low nitrogen starting material) were particularly high in phenol, $C_1$ and $C_2$-substituted phenols, $C_{10}$ to $C_{25}$ alkanes, toluene, and $C_2$-substituted dihydro-1H-indenes.

Reaction products from cellulose (a low nitrogen starting material) were particularly high in phenol, $C_1$ and $C_2$-substituted phenols, $C_2$ to $C_4$-substituted benzenes, cyclopentanone, and $C_1$-substituted naphthalenes.

Reaction products from lignin (a low nitrogen starting material) were particularly high in phenol, $C_1$ to $C_3$-substituted phenols, $C_1$ to $C_3$-substituted benzenes, 2-naphthol, $C_1$ and $C_2$-substituted naphthalenes, and $C_1$-substituted 1H-indenes.

Reaction products from DNA (a high nitrogen starting material) were particularly high in phenylethanone, dihydro-1H-indenone, and phenol.

Reaction products from *P. spartinae* (a high nitrogen starting material) were particularly high in phenol, $C_2$-substituted cyclopentanones, $C_1$ and $C_2$-substituted phenols, $C_2$ and $C_3$-substituted benzenes, and $C_{13}$-alkanes.

Reaction products from cytochrome C (a high nitrogen starting material) were particularly high in phenol, toluene, phenylethanone, $C_1$-pyridines, and 1H-indole.

TABLE 1

C, H, N, S Elemental Composition of Various Biomass Starting Materials

| Material | % C | % H | % N | % S |
|---|---|---|---|---|
| Chitin | 43.07 (0.3) | 6.50 (1.4) | 6.46 (0.8) | 0.87 (4.1) |
| Starch | 38.95 (0.1) | 6.48 (0.8) | 0.00 (0.0) | 0.87 (6.2) |
| Humic Acid | 39.14 (0.2) | 4.17 (2.5) | 0.66 (1.1) | 0.61 (9.3) |
| Lignin | 63.37 (0.5) | 5.72 (1.6) | 0.77 (0.84) | 0.79 (6.5) |
| Cytochrome c | 47.83 (0.2) | 6.92 (0.3) | 14.95 (0.7) | 1.72 (4.5) |
| Cellulose | 38.54 (0.2) | 6.54 (0.7) | 0.00 (0.0) | 0.75 (6.5) |
| S. alterniflora | 37.40 (1.4) | 5.45 (2.9) | 1.23 (1.02) | 0.73 (5.6) |
| P. spartinae | 42.09 (0.2) | 6.23 (0.8) | 10.93 (0.5) | 0.96 (5.4) |
| T. weissflogii | 7.14 (0.3) | 3.06 (0.07) | 1.30 (0.07) | 1.17 (0.01) |
| Corn Oil | 76.79 (0.05) | 11.44 (0.09) | 0.85 (0.09) | 1.52 (0.06) |

Notes to Table 1:
Data shown are means ($\mu$) and standard deviations ($\sigma$) for n = 3 replicate analyses.
S. alterniflora is a salt marsh cord grass.
P. spartinae is a yeast.
T. weissflogii is a phytoplankton.

TABLE 2

C, H, N Elemental Composition of Corn Oil Starting Material and End Products

| Material | % C | % H | % N | C:H mass ratio |
|---|---|---|---|---|
| Corn Oil Starting Material | 76.79 (0.05) | 11.44 (0.09) | 0.85 (0.09) | 6.71 |
| Corn Oil in near critical water, 4 hours under Argon (~1300 psi) | 78.44 (0.18) | 11.78 (0.18) | 0.23 (0.14) | 6.66 |
| Corn Oil in near critical water, 4 hours under $H_2$ gas (~1300 psi) | 72.92 (2.24) | 10.43 (0.73) | 0.26 (0.30) | 7.00 |

Note to Table 2:
Data shown are means ($\mu$) and standard deviations ($\sigma$) for n = 3 replicate analyses.

The data shown in Table 2 suggest that the degree of hydrogenation was substantially greater with hydrogen than with argon. Further work is being conducted to confirm this observation. Without wishing to be bound by this theory, it is believed that the increased variance in the elemental analyses for the sample under hydrogen resulted from the higher production of volatile products.

Reaction variables that can be optimized in the conversion of particular starting materials include shaking or stirring the reaction mixture, using a multi-reactor flow-through process, using co-reactants such as reduced metals, changing the concentration of reactants, reacting under a hydrogen atmosphere, using thermal cycles, and using hot zone-cold zone fractionation.

As used in the specification and the claims, the term "essentially free of any strong oxidant" refers to reaction conditions that are devoid of any strong oxidizing agent, or to reaction conditions where the concentration of any strong oxidizing agent that may be present is insufficient to alter substantially the composition of the products of the reaction as compared to the products of an otherwise identical reaction of starting materials that are otherwise identical, except that the starting materials are completely devoid of strong oxidizing agents.

As used in the specification and claims, the term "biomass" refers to a material of biological origin, that has a substantial fraction of carbon and hydrogen other than in carbonate or hydrocarbon form. The presence of carbonate and hydrocarbons is not excluded; however, there must be a substantial fraction of carbon and hydrogen in a form other than carbonate or hydrocarbon. The presence of nitrogen, sulfur, and other constituents in the biomass is acceptable; in experiments to date, the presence of these other constituents has only slightly affected the outcome.

As used in the specification and claims, the term "hydrocarbon mixture" refers to a mixture that contains a substantial fraction of hydrocarbons (alkanes, alkenes, aromatics, aliphatics). The presence of compounds in the mixture other than hydrocarbons is not excluded, however.

As used in the specification and claims, "supercritical" conditions refer to reaction conditions where both the temperature is greater than 374.2° C. and the pressure is greater than 221 bar. As used in the specification and claims, "near critical conditions" refer to conditions that do not satisfy this definition of "supercritical," but where both the temperature is greater than about 320° C., and the pressure is greater than about 200 bar.

As used in the specification and claims, a "reactor" for a process is any device or vessel that is supplied by the operator of the process, and in which the chemical reactions of the process may take place.

The complete disclosures of all references cited in this specification are hereby incorporated by reference. In the event of an otherwise irreconcilable conflict, however, the present specification shall control.

We claim:

1. A process for converting biomass to a hydrocarbon mixture, said process comprising reacting the biomass with water in a reactor at a temperature greater than about 320° C. and a pressure greater than about 200 bar, under reaction conditions that are essentially free of any strong oxidant, for a time sufficient to convert a substantial portion of the biomass to hydrocarbons.

2. A process as recited in claim 1, wherein the process is performed under supercritical conditions.

3. A process as recited in claim 1, wherein the process is performed under near critical conditions.

4. A process as recited in claim 1, wherein said reacting step occurs in the presence of a noble gas.

5. A process as recited in claim 1, wherein said reacting step occurs in the presence of a reducing agent.

6. A process as recited in claim 1, wherein said reacting step occurs in the presence of elemental hydrogen.

7. A process as recited in claim 1, wherein said reacting step occurs in the presence of borohydride.

8. A process as recited in claim 1, wherein said reacting step occurs in the presence of at least one reduced metal.

9. A process as recited in claim 1, wherein said reacting step occurs in the presence of reduced copper.

10. A process as recited in claim 1, wherein the biomass is selected from the group consisting of cellulose, chitin, starches, lipids, proteins, lignin, whole cells, seed oils, food processing wastes, seafood industry wastes, paper manufacturing byproducts, wood industry manufacturing by-products, leaves, grass clippings, rice hulls, bagasse, seaweed, milling waste, cotton waste, and animal waste.

11. A hydrocarbon mixture produced by the process of claim 1.

12. A hydrocarbon mixture produced by the process of claim 2.

13. A hydrocarbon mixture produced by the process of claim 3.

14. A hydrocarbon mixture produced by the process of claim 4.

15. A hydrocarbon mixture produced by the process of claim 5.

16. A hydrocarbon mixture produced by the process of claim 6.

17. A hydrocarbon mixture produced by the process of claim 7.

18. A hydrocarbon mixture produced by the process of claim 8.

19. A hydrocarbon mixture produced by the process of claim 9.

20. A hydrocarbon mixture produced by the process of claim 10.

* * * * *